United States Patent [19]

DeGraw et al.

[11] Patent Number: 5,167,963
[45] Date of Patent: Dec. 1, 1992

[54] 8,10-DIDEAZATETRAHYDROFOLIC ACID DERIVATIVES

[75] Inventors: Joseph I. DeGraw, Sunnyvale; William T. Colwell, Menlo Park, both of Calif.; Francis M. Sirotnak, New York, N.Y.

[73] Assignees: SRI International, Menlo Park, Calif.; Sloan Kettering Institute for Cancer Research, New York, N.Y.

[21] Appl. No.: 558,923

[22] Filed: Jul. 27, 1990

Related U.S. Application Data

[63] Continuation-in-part of Ser. No. 245,831, Sep. 16, 1988, abandoned.

[51] Int. Cl.$^5$ .................. A61K 9/02; A61K 9/64; A61K 31/495; C07D 471/04
[52] U.S. Cl. .................. 424/436; 424/408; 424/456; 424/464; 424/DIG. 15; 514/258; 514/937; 514/944; 514/960; 514/962; 514/966; 544/260; 544/279
[58] Field of Search .............. 424/408, 423, 436, 456, 424/464, DIG. 15; 514/258, 937, 944, 960, 962, 966; 544/260, 279

[56] References Cited

U.S. PATENT DOCUMENTS 4,684,653 8/1987 Taylor et al. .................. 514/258

OTHER PUBLICATIONS

"Synthesis and Biological Activity of L-5-Deazafolic Acid and L-5-Deazaaminopterin: Synthetic Strategies to 5-Deazapteridine's"; Taylor et al., Journal of Organic Chemistry, pp. 4852-4860, 1983.

Primary Examiner—Thurman K. Page
Assistant Examiner—C. Azpuru

[57] ABSTRACT 8,10-Dideazatetrahydrofolic acid derivatives of the formula:

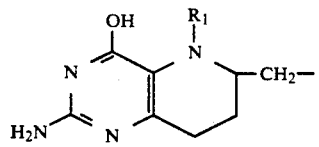

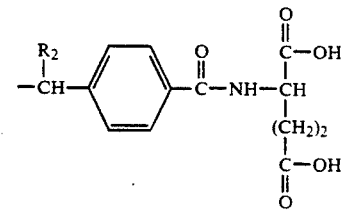

where $R_1$ and $R_2$ are selected from hydrogen and alkyl having from one to about eight carbon atoms and the carboxylates and acid addition salts thereof, showing strong inhibition of L1210 murine leukemia cells in culture, modest inhibition of glycinamide ribotide transformylase and aminoimidazole carboxamide ribotide transferase, and insignificant inhibition of dihydrofolate reductase and thymidylate synthase enzymes.

20 Claims, No Drawings

8,10-DIDEAZATETRAHYDROFOLIC ACID DERIVATIVES

ORIGIN OF INVENTION

The invention described herein was in part made in the course of work under a grant or award from the National Institute of Health, Department of Health, Education and Welfare.

This application is a continuation-in-part of Ser. No. 245,831, filed Sep. 16, 1988, and now abandoned.

Mead, U.S. Pat. No. 3,856,959, patented Dec. 24, 1974, provides a method of inhibiting methotrexate-sensitive leukemia L1210 and methotrexate-resistant leukemias derived from L1210, such as variants L1210/FR-8, L1210/M-46-R, L1210/C-95, and L1210/M-66-3A in mice, employing 5-methyltetrahydrohomofolate utilized as an injectable in a dosage regimen of 12.5–1600 mg/kg/inj/diem.

Mead notes that

In modern leukemia therapy, the standard drug of comparison for several years has been methotrexate (amethopterin). The modus of action in vivo of this compound in enzymatic reaction is to inhibit the action of dihydrofolate reductase and this and similar drugs constituting 4-amino analogues of folic acid are known as the 4-amino-antifolates. It has recently been realized that where leukemia is strongly resistant to the 4-amino-antifolates and is characterized by high levels of dihydrofolate reductase, certain homofolate derivatives show a substantial antileukemic effect—J. A. R. Mead, Ann. New York Acad. Sci., 186, 514–515, November, 1971.

It has been shown that tetrahydrohomofolate is a potent inhibitor in vitro in the enzymatic reaction of thymidylate synthetase and the enzyme is metabolically beyond or below the action of the dihydrofolate reductase. Thus, it is considered possible that dihydrohomofolate and possibly homofolate by conversion in vivo to a specific inhibitor of thymidylate synthesis might block the growth of amethopterin-resistant cells having high levels of dihydrofolate reductase—J. A. R. Mead et al., Cancer Research, 2374–2379 (1966).

Whereas the known compounds utilized have been active at (2) in Mead's Chart I, the tetrahydrohomofolates are active at (3), and Mead believed 5-methyltetrahydrohomofolate (5-MeTHHF) is active at (4) relative to the action of methionine synthetase.

CHART 1
Enzymic Reactions of Folates

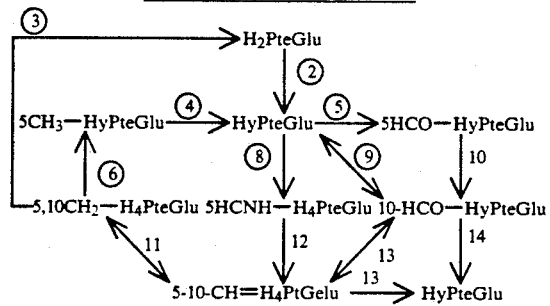

(1) Conjugase

-continued
CHART 1
Enzymic Reactions of Folates (2) Dihydrofolate reductase
(3) Thymidylate synthetase
(4) Methionine synthetase
(5) Formylglutamate formyl transferase
(6) $N_5$, $N_{10}$-methylenetetrahydrofolate reductase
(7) L-Serine hydroxymethyl transferase
(8) Formiminoglutamate Formimino Transferase
(9) $N_{10}$-fromyltetrahydrofolate synthetase
(10) $N_5$-formyltetrahydrofolate isomerase
(11) $N_5$, $N_{10}$-methylenetetrahydrofolate dehydrogenase
(12) $N_5$-formiminotetrahydrofolate cyclodeaminase
(13) $N_5$, $N_{10}$-methenyltetrahydrofolate cyclohydrolase
(14) 5-Amino-4-imidazole carboxamide ribonucleotide transformylase
(15) Glycinamide ribonucleotide transformylase 5-Methyl tetrahydrohomofolate has the formula

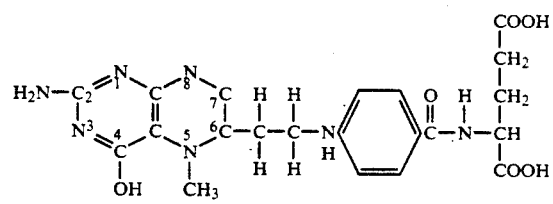

DeGraw, Jr. et al, U.S. Pat. No. 4,369,319, patented Jan. 18, 1983, provides a process and composition employing 10-deazaminopterin and 10-alkyl derivatives thereof for the treatment of leukemia, as well as other tumor systems including those of ascitic character, and also a process for preparing 10-deazaminopterin compounds.

These 10-deazaminopterin compounds have the structure:

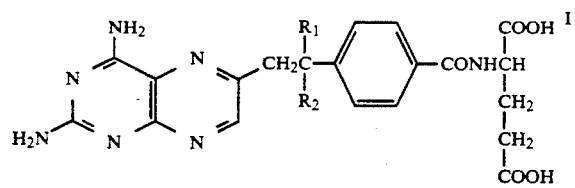

In the compound 10-deazaminopterin, $R_1$ and $R_2$ are both hydrogen. In the alkyl derivatives, either or both of $R_1$ and $R_2$ can be alkyl having from one to about eight, preferably one or two carbon atoms. When only one of $R_1$ and $R_2$ is alkyl, the other is hydrogen.

Temple et al, U.S. Pat. No. 4,431,805, patented Feb. 14, 1984, report that the 5-deaza analogs of folic acid, $N^{10}$-methylfolic acid, aminopterin, methotrexate and the diethyl ester of aminopterin, inhibit the growth of human epidermoid carcinoma cells No. 2 and are active against leukemia in laboratory animals. The 5-deaza analogs of folic acid, $N^{10}$-methylfolic acid, aminopterin and methotrexate have the following structures:

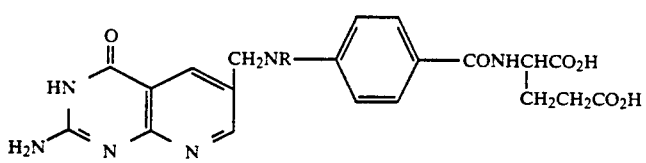

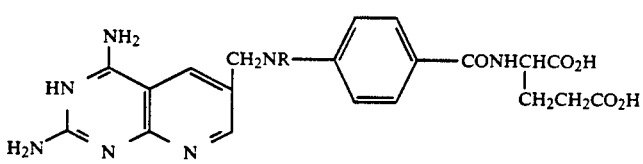

wherein R is either hydrogen or methyl.

DeGraw et al, U.S. Pat. No. 4,460,591, patented Jul. 17, 1984, and 4,532,241, patented Jul. 30, 1985, provide 10-alkyl-8,10-dideazaminopterins of the formula:

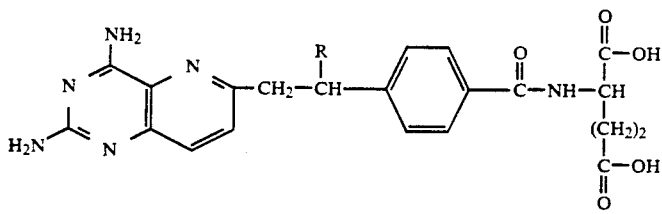

where R is hydrogen or alkyl of 1 to about 8 carbon and their carboxylate and acid addition salts are described. These compounds exhibit antineoplastic activity that is similar to, but more effective than, methotrexate.

DeGraw et al note that

Aminopterin and its N-10-methyl derivative, methotrexate, have long been recognized as powerful antineoplastic agents. Methotrexate has enjoyed some thirty years of acceptance as a clinically useful anticancer drug. The drugs are antimetabolites inhibiting dihydrofolate reductase (DHFR). They affect both neoplastic and normal host tissue.

Alterations of the pteridine ring of folic acid have also been investigated. The synthesis and antifolate activity of 8-deazafolic acid was reported by J. I. DeGraw, R. L. Kisliuk, Y. Gaumont and C. M. Baugh J Med Chem, 17, 470 (1974) and 8,10-dideazafolic acid was reported in J. I. DeGraw, R. L. Kisliuk, V. H. Brown and Y. Gaumont, ("em Biol Pteridines, 6, 229 (1979). Both of these compounds were active antifolates, but did not significantly affect DHFR. A. Srinivasan and A. D. Broom, J Org Chem, 46, 1777 (1981) reported the preparation of 8-deazaminopterin and 8-deazamethotrexate, but did not report biological activity for the compounds.

Temple et al, U.S. Pat. Nos. 4,526,964, patented Jul. 2, 1985, and 4,536,575, patented Aug. 20, 1985, indicate that The 5-deaza analogs of folic acid, $N^{10}$-substituted folic acid, aminopterin, $N^{10}$-substituted aminopterin and the diethyl ester of aminopterin inhibit the growth of human epidermoid carcinoma cells No. 2 and are active against leukemia in laboratory animals. The 5-deaza analogs of folic acid and $N^{10}$-substituted folic acid referred to herein have the following structure:

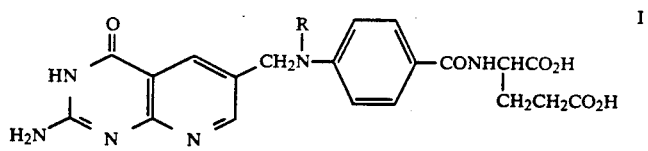

and the 5-deaza analogs of aminopterin and $N^{10}$-substituted aminopterin referred to herein have the following structure:

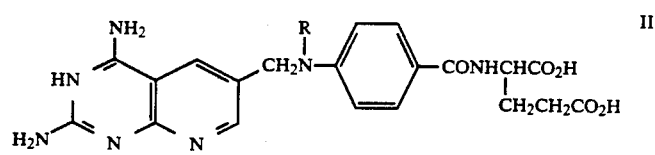

wherein R is hydrogen, $CH_3$, $CH_3CH_2$, $CH_3CH_2CH_2$, $CH_2=CHCH_2$ or $CH=CCH_2$.

Taylor et al, U.S. Pat. No. 4,684,653, patented Aug. 4, 1987, provides (ia) pyrido[2,3-d]pyrimidines of the formula:

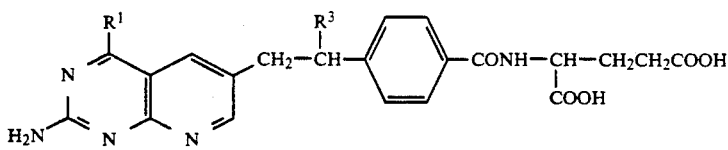

IA wherein
R$^1$ is amino or hydroxy; and
R$^3$ is hydrogen, methyl, or ethyl; the configuration about the carbon atom designated * being L;
(ib) 5,6,7,8-tetrahydropyrido[2,3-d]-pyrimidines of the formula:

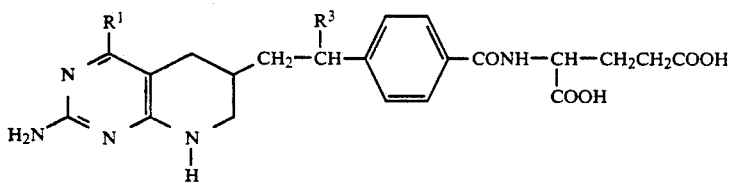

IB wherein
R$^1$ is amino or hydroxy; and
R$^3$ is hydrogen, methyl, or ethyl; the configuration about the carbon atom designated * being L;
(ii) the tautomeric forms thereof; and
(iii) the pharmaceutically acceptable alkali metal, alkaline earth metal, non-toxic metal, ammonium, and substituted ammonium salts thereof.

These compounds are antineoplastic agents, and have an effect on one or more enzymes which utilize folic acid, and in particular metabolic derivatives of folic acid, as a substrate, including dihydrofolate reductase, thymidylate syntheiase and folate polyglutamate syntheiase.

N-(4-[2-(2-amino-4-hydroxy-5,6,7,8-tetrahydropyrido[2,3-d]pyrimidin-6-yl)-ethyl]benzoyl)-L-glutamic acid in particular is a unique antimetabolite. While maintaining good activity against L-1210 leukemia which is comparable to methotrexate, the compound is a weak inhibitor of dihydrofolate reductase, indicating probable activity against the folate-related enzyme targets other than DHFR.

Taylor et al *The Journal of Organic Chemistry* (1983) Vol. 48, No. 25, pp. 4852–4860 discloses pyrimidines of the formula:

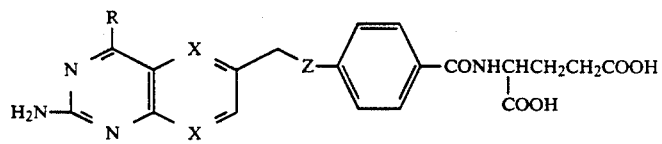

1, R = NH$_2$, X = Y = N, Z = NCH$_3$
2, R = NH$_2$, X = Y = N, Z = NH
3, R = OH, X = CH, Y = N, Z = NH
4, R = OH, X = Y = N, Z = CH$_2$
5, R = NH$_2$, X = Y = N, Z = CH$_2$
6, R = NH$_2$, X = N, Y = CH, Z = NH
7, R = OH, X = Y = CH, Z = NH
8, R = NH$_2$, X = Y = CH, Z = NH
9, R = OH, X = CH, Y = N, Z = CH$_2$
10, R = OH, X = Y = CH, Z = CH$_2$
11, R = NH$_2$, X = Y = CH, Z = CH$_2$
12, R = OH, X = N, Y = CH, Z = NH

No 5,6,7,8-tetrahydropyrido[2,3-d]pyrimidines are disclosed.

The Taylor article was published in 1983, whereas the Taylor patent issued in 1987, and is based on applications filed in 1985 and 1986, two years later than the article. The patent disclosure shows significant changes in thinking from the article.

Firstly, the patent introduces 5,6,7,8-tetrahydropyrido compounds into the scheme. At the same time, the patent withdraws all compounds having a Y group (see the formula in the article, reproduced above, at page 4. All the patented compounds have no Y group but only the X group in the 8-position. The patent thus corrects such a group at the 8-position.

Secondly, whereas the patented Taylor compounds have the group CH$_2$CHR$^3$ linking the glutamic acid group to the 7-position of the pyridine ring, the compounds of the Taylor article have a CH$_2$Z group in this position, and Z can be not only CH$_2$ but also NCH$_3$ and CHCH$_2$ while it certainly cannot be CH$_2$CHR$^3$, where R$^3$ is methyl or ethyl. Again, the patent backs off the article's scope for Z. Thus, the Taylor patent narrows the Z scope of the article, thus warning those skilled in the art that extrapolation from its disclosure is dangerous, and unpredictable in result.

In accordance with the present invention, 8,10-dideazatetrahydrofolic acid derivatives are provided of Exemplary 8,10-dideazatetrahydrofolic acid derivatives falling within the invention include:

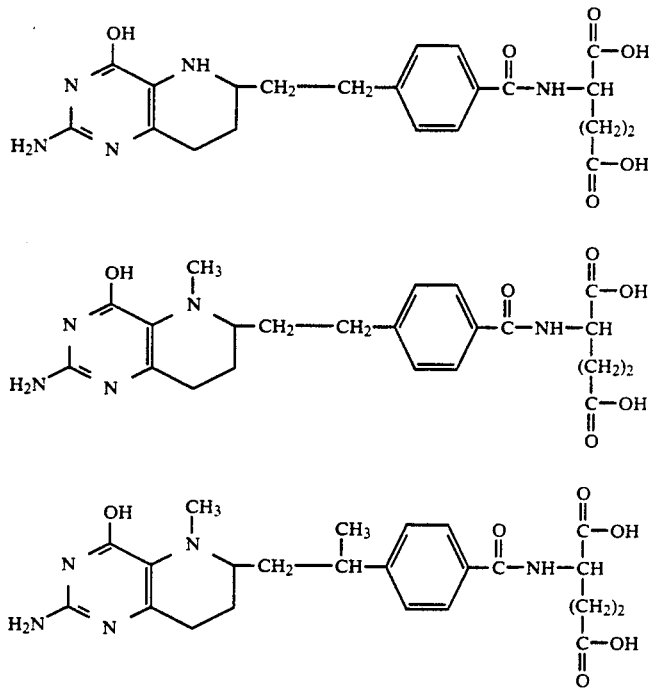

the formula:

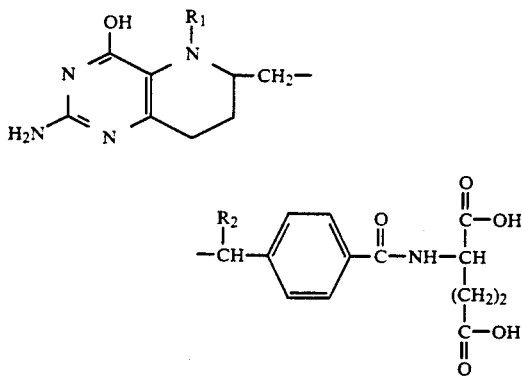

where $R_1$ and $R_2$ are selected from hydrogen and alkyl having from one to about eight carbon atoms and the carboxylates and acid addition salts thereof.

These compounds, unlike prior folic acid derivatives, such as 2,4-diamino antifolates, and 5-methyltetrahydrohomofolate, they show only insignificant inhibition of dihydrofolate reductase and thymidylate synthase enzymes, and it is accordingly surprising that they show strong inhibition of L1210 murine leukemia cells in culture, and modest inhibition of glycinamide ribotide transformylase and aminoimidazole carboxamide ribotide transferase.

and the carboxylate and acid addition salts thereof.

In accordance with the invention, the 8,10-dideazatetrahydrofolic acid derivatives of Formula I are provided as new compounds, with distinctive and valuable properties, for example, significantly effective in the inhibition of growth of L1210 murine leukemia cells.

Also in accordance with this invention, a synthesis is provided that affords 8,10-dideazatetrahydro folic acid derivatives of Formula I.

Accordingly, these 8,10-dideazatetrahydro folic acid derivatives are expected to have utility in the treatment of human cancer.

The invention accordingly also provides a process of treating leukemia and ascitic tumors, which comprises administering to a warm-blooded animal having an abnormal proportion of leukocytes or other evidences of the malignancy, a therapeutic nontoxic amount of an 8,10-dideazatetrahydro folic acid derivative of Formula I, as such or in the form of a pharmaceutically acceptable carboxylate or acid addition salt thereof. The carboxylates are formed by neutralization of one or both COOH groups, and the addition salts are formed with one or more free $NH_2$ groups of the 8,10-dideazatetrahydro folic acid derivative.

The process of the invention for the preparation of the 8,10-dideazatetrahydro folic acid derivative is a synthesis including the following steps, exemplified by $R_1$ as methyl $CH_3$ and $R_2$ as hydrogen.

Stage 1

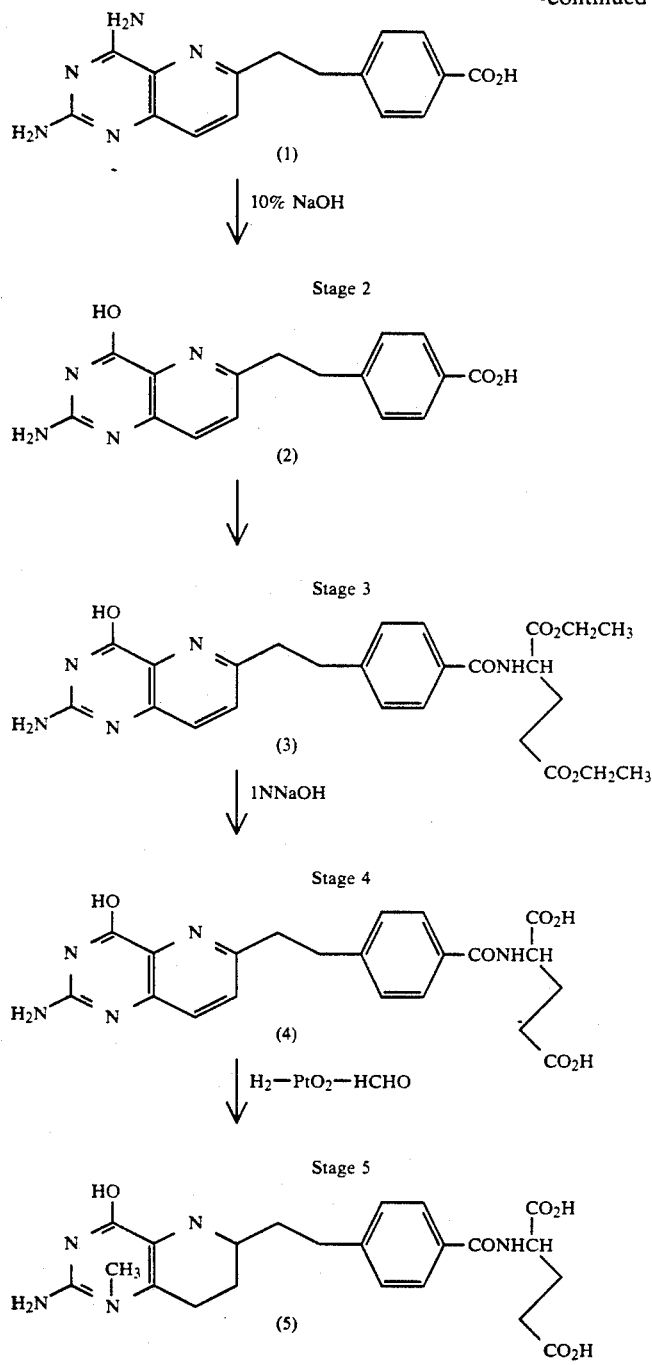

As the synthesis scheme shows, hydrolysis of the 2,4-diamino-4-deoxy-8,10-dideazapteroic acid (1) with hot 10% NaOH effects displacement of the 4-NH$_2$ group to 4-OH yielding 8,10-dideazapteroic acid (2). Compound 2 is coupled with diethyl L-glutamate with activation of the benzoate carboxyl group as the mixed anhydride formed by isobutyl chloroformate to afford diethyl 8,10-dideazafolate (3). Saponification of the diester (3) in 2-methoxyethanol containing 1N NaOH yields 8,10-dideazafolic acid (4). Hydrogenation of 4 over a platinum catalyst in the presence of an equivalent of formaldehyde in an acidic medium afford 5-N-methyltetrahydro-8,10-dideazafolic acid (5).

Hydrogenation of the folic acid intermediate (4) in the absence of formaldehyde yields tetrahydro-8,10-dideazafolic acid itself, R$_1$ and R$_2$=H.

Substitution of other alkyl groups for R$_1$ and R$_2$ in the above scheme are apparent to those skilled in the art, with combinations of either hydrogen and alkyl or different alkyls as R$_1$ and R$_2$.

In Stage 1, the hydrolysis of the 4-amino group of the pyrimidine ring may be carried out by treatment with any appropriate alkali metal hydroxide at temperatures of 50°–150° C. The hydrolysis may also be conducted in strongly acidic media such as mineral acids at similar temperatures. If 10-alkyl substituted analogs of formula (1), where R$_2$=alkyl, are employed the products at Stage 1 and subsequent stages will bear the 10-alkyl substituent.

In Stage 2, the benzoic acid moiety is activated by conversion to a mixed anhydride by treatment of its triethylamine salt with isobutyl chloroformate in a polar organic solvent. Other organic tertiary amine bases such as tributylamine, N-methyl morpholine, collidine can be employed as can other esters of chloroformic acid. The mixed anhydride is allowed to react with diethyl L-glutamate at ordinary temperatures and the product is best purified by chromatography on silica gel.

In Stage 3, hydrolysis of the esterifying groups is carried out with aqueous alkali at room temperature or above. The diester can be dissolved in a suitable solvent, such as 2-methoxyethanol, and held in the presence of the aqueous alkali until hydrolysis is complete. The hydrolysis product folic acid analog can then be precipitated by addition of acid such as acetic or hydrochloric. The precipitate can be recovered, washed and dried.

In Stage 5, the substrate folic acid analog is hydrogenated at room temperature and atmospheric pressure in an aqueous acid medium, preferably containing acetic acid as a cosolvent. A catalyst such as platinum oxide or palladium may be employed. To obtain a 5-N-alkyl product via reductive alkylation it is necessary to incorporate an equivalent of the appropriate aldehyde such as formaldehyde, acetaldehyde, etc. If the aldehyde reagent is deleted one obtains the target compounds containing an NH at the 5-position.

The following is illustrative of the procedure:

EXAMPLE

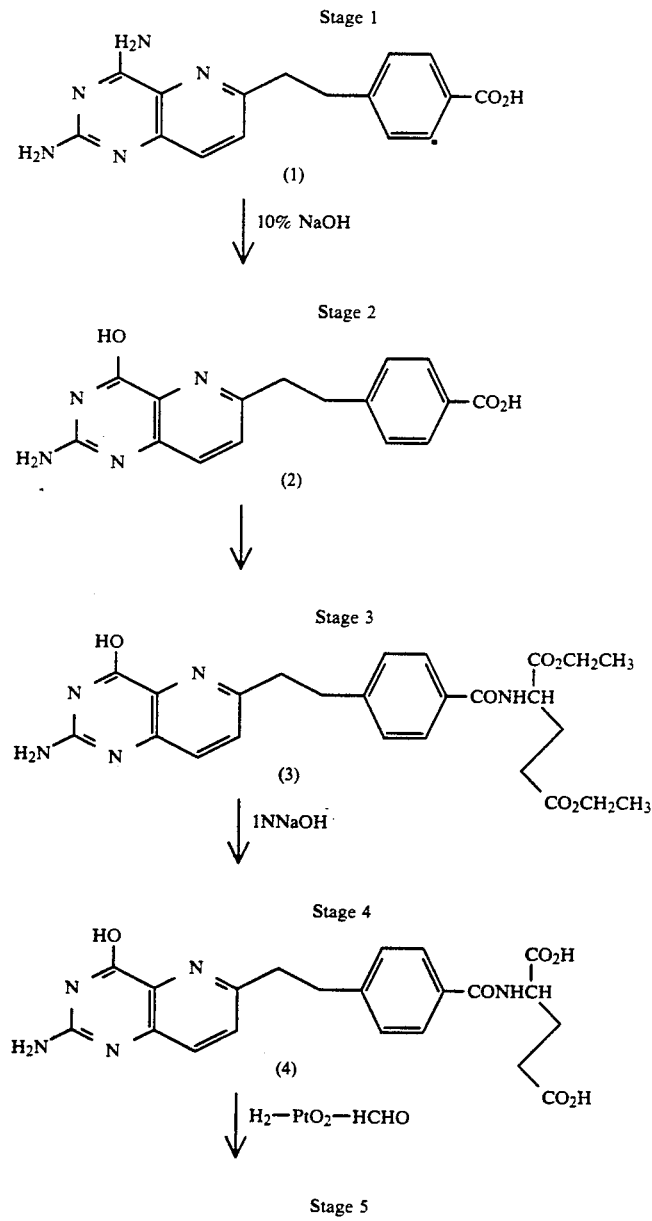

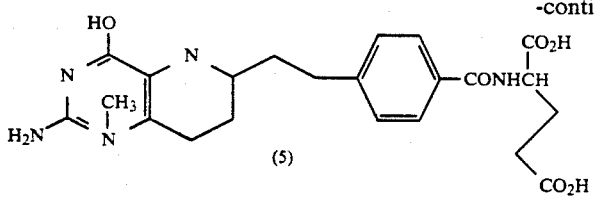

(5)

8,10-Dideazapteroic Acid (2)

2,4-Diamino-4-deoxy-8,10-dideazapteroic acid (1) 0.88 g, 2.8 mmol, was heated to 85°–90° with 15 ml of 10% NaOH solution under an argon atmosphere. HPLC analysis of the reaction indicated maximum conversion after 5 hours. The reaction mixture was cooled to 5° for 48 hours. The resulting ppt. (di-sodium salt) was collected and washed with a small amount of ice-cold 10% NaOH solution. The ppt. was stirred with a little $H_2O$ and the pH adjusted to 5 by addition of HOAc. The suspended solid was stirred for 10 minutes, then collected and washed with a little $H_2O$ to yield 0.52 g of light grey solid after drying. Mass spectrum, m/e 310 (calc'd. 310). Anal. calc'd. for $C_{16}H_{14}N_4O_3.0.5-H_2O$: C, 60.2; H, 4.42; N, 17.5. Found: C, 60.2; H, 4.51; N, 17.5.

8,10-Dideazafolic Acid, Diethyl Ester (3).

8,10-Dideazapteroic acid (2) 0.52 g, 1.7 mmol was stirred with 15 ml of dry DMF under an argon atmosphere. Triethylamine (0.69 g, 6.8 mmol) was added and the mixture stirred for 15 minutes, then isobutyl chloroformate (0.87 g, 6.4 mmol) was added. After 1 hour only partial solution was obtained. The reaction was sequentially treated with triethylamine (0.017 g, 1.7 mmol) and isobutyl chloroformate (0.23 g, 1.7 mmol). Complete solution occurred after 20 minutes. Triethylamine (0.81 g, 8.1 mmol) followed by diethyl-L-glutamic acid diethyl ester in 10 ml of DMF were added and the resulting solution was stirred for 20 hours. The solvent was removed at 40° (0.1 mm) and the residue was dissolved in $CHCl_3$ then washed with $H_2O$ and dilute $NH_4OH$, dried and the solution evaporated in vacuo. The gummy residue was chromatographed on silica gel with $CHCl_3$ and $CH_3OH—CHCl_3$ elution. The product, 110 mg of yellow solid, was eluted with $CH_3OH:CHCl_3$, 2:98. Anal. calc'd for $C_{25}H_{29}N_5O_6.0.5H_2O$: C, 59.5; H, 5.99; N, 13.9. Found: C, 59.3; H, 5.80; N, 13.6.

8,10-Dideazafolic Acid (4)

8,10-Dideazafolic acid diethyl ester (3) 110 mg, 0.22 mmol, was treated with 1 ml of 1N NaOH solution. and 1 ml of 2-methoxyethanol. The solution was stirred for 15 hours then the solvents were removed at 40° (0.1 mm). The residue was treated with 1 ml of $H_2O$ and acidified to pH 5.5 with HOAc. The resulting ppt. was collected, washed with $H_2O$ and dried to yield 74 mg of product as a yellow solid. Anal. calc'd. for $C_{21}H_{21}N_5O_6.2H_2O$: C, 53.1; H, 5.30; N, 14.7. Found: C, 53.4; H, 4.67; N, 14.5.

5-Methyl-8,10-dideaza-5,6,7,8-tetrahydrofolic Acid (5)

8,10-Dideazafolic acid (4) 74 mg, 0.17 mmol was dissolved in 8 ml of acetic acid and 2 ml of $H_2O$ containing 0.24 mmol of HCl. $PtO_2$ (24 mg) was added and the mixture was hydrogenated at atmospheric pressure. Hydrogen uptake ceased after uptake of 15 ml $H_2$ (theory 12.4 ml) and formaldehyde (0.018 ml, 0.20 mmol, of 35% formaldehyde) was added. Continued hydrogenation resulted in the rapid uptake of 4 ml of $H_2$ (theory 3.8 ml). The mixture was filtered through Celite and the solvent removed at 40° (0.1 mm). The residue was twice treated with 2 ml of $H_2O$ and taken to dryness each time to leave 90 mg of white solid. Mass spectrum, m/e (TMS) 457 (calc'd. 457). Anal. calc'd for $C_{22}H_{28}N_5O_6Cl.H_2O$: C, 51.6; H, 5.90; N, 13.6. Found: C, 51.4; H, 5.82; N, 13.2.

8,10-Dideaza-5,6,7,8-tetrahydrofolic Acid 8,10-Dideazafolic acid (4) 100 mg, 0.23 mmol dissolved in 10 ml of HOAc, 9 ml $H_2O$, and 2 ml (0.24 mmol) of HCl solution was hydrogenated at atmospheric pressure over 25 mg of $PtO_2$. After 1 hour, 15 ml of $H_2$ (theory 15 ml) had been taken up. The mixture was filtered through Celite then taken to dryness at 0.1 mm pressure (40°). The residue was twice treated with 10 ml $H_2O$ and taken to dryness each time to yield 100 mg of white solid. Mass spectrum m/e 443 (calc'd. 443).

The 8,10-dideazatetrahydro folic acid can be administered per se, or in association with a pharmaceutically acceptable diluent or carrier. The invention accordingly also provides a pharmaceutical composition in dosage unit form comprising from 0.1 to about 500 mg of 8,10-dideazatetrahydro folic acid per dosage unit, together with a pharmaceutically acceptable nontoxic inert carrier or diluent therefor.

The 8,10-dideazatetrahydro folic acid can be used as such, or in the form of their carboxylates or an acid addition salt. The carboxylates are formed by neutralization of one or two of the COOH groups with an alkali metal or alkaline earth metal or ammonia or a lower aliphatic amine. The acid addition salts are formed with one or more free $NH_2$ groups of the tetrahydro folic acid molecule.

The acid addition salts are preferably the pharmaceutically acceptable, nontoxic addition salts with suitable acids, such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicyclic, o-acetyloxybenzoic, nicotinic and isonicotinic acid, and organic sulphonic acids, for example, methanesulphonic, ethanesulphonic, 2-hydroxyethanesulphonic, toluene-p-sulphonic, and naphthalene-2-sulphonic acid.

An acid addition salt can be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate; with ammonia; or with a hydroxyl ion exchange resin, or with any other suitable reagent.

An acid addition salt may also be converted into another acid addition salt according to known methods; for example, a salt with an inorganic acid may be treated with a metal salt, for example a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation.

The 8,10-dideazatetrahydro folic acid or carboxylate or salt thereof can be administered to the animal by any available route, including oral and parenteral (intravenous, intraperitoneal, subcutaneous, and intramuscular) administration. The amount administered is sufficient to ameliorate the leukemia or the ascitic tumor, and will depend upon the type of leukemia, the species of animal, and the weight of the animal. For example, in human administration, a dosage of 8,10-dideazatetrahydro folic acid within the range of from about 0.1 mg/kg or about 500 mg/kg per day should be sufficient. Dosages in the higher part of the range, approaching 500 mg/kg, are normally administered in conjunction with leucovoran (di-5-formyl tetrahydrofolate) to reduce toxicity. In the treatment of lower test animals, a similar dosage range is therapeutic. The upper limit of dosage is that imposed by toxic side effects, and can be determined by trial and error for the animal to be treated, including humans.

To facilitate administration, the 8,10-dideazatetrahydro folic acid or carboxylate or salt thereof can be provided in composition form, and preferably in dosage unit form. While the compound can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and non-toxic.

The carrier or diluent can be solid, semisolid, or liquid, and can serve as a vehicle, excipient, or medium for the 8,10-dideazatetrahydro folic acid. Exemplary diluents and carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl- and propylhydroxybenzoate, talc or magnesium stearate.

For convenience in handling, the 8,10-dideazatetrahydro folic acid and carrier or diluent can be enclosed or encapsulated in a capsule, sachet, cachet, gelatin, paper or other container, especially when intended for use in dosage units. The dosage units can for example take the form of tablets, capsules, suppositories or cachets.

The following Examples illustrate various forms of dosage units in which the 8,10-dideazatetrahydro folic acid or carboxylates or salts thereof can be prepared.

| Tablet formulation | Mg/tablet |
| --- | --- |
| 8, 10-dideazatetrahydro folic acid | 15 |
| Lactose | 86 |
| Corn starch (dried) | 45.5 |
| Gelatin | 2.5 |
| Magnesium stearate | 1.0 |

The 8,10-dideazatetrahydro folic acid is powdered and passed through a mesh sieve and well mixed with the lactose and 30 mg of the corn starch, both passed through a sieve.

The mixed powders are massed with a warm gelatin solution, prepared by stirring the gelatin in water and heating to form a 10% w/w solution. The mass is granulated by passing through a sieve, and the moist granules dried at 40° C.

The dried granules are regranulated by passing through a sieve and the balance of the starch and the magnesium stearate is added and thoroughly mixed.

The granules are compressed to produce tablets each weighing 150 mg.

EXAMPLE 2

| Tablet formulation | Mg/tablet |
| --- | --- |
| 8, 10-dideazatetrahydro folic acid | 100 |
| Lactose | 39 |
| Corn starch (dried) | 80 |
| Gelatin | 4.0 |
| Magnesium stearate | 2.0 |

The method of preparation is identical with that of Example 1 except that 60 mg of starch is used in the granulation process and 20 mg during tabletting.

EXAMPLE 3

| Capsule formulation | Mg/capsule |
| --- | --- |
| 8, 10-dideazatetrahydro folic acid | 250 |
| Lactose | 150 |

The 8,10-dideazatetrahydro folic acid and lactose are passed through a sieve and the powders well mixed together before filling into hard gelatin capsules of suitable size, so that each capsule contains 400 mg of mixed powders.

EXAMPLE 4

| Suppositories | Mg/suppositories |
| --- | --- |
| 8, 10-dideazatetrahydro folic acid | 50 |
| Oil of Theobroma | 950 |

The 8,10-dideazatetrahydro folic acid is powdered and passed through a sieve and triturated with molten oil of theobroma at 45° C. to form a smooth suspension.

The mixture is well stirred and poured into molds, each of nominal 1 g capacity, to produce suppositories.

EXAMPLE 5

| Cachets | Mg/cachet |
| --- | --- |
| 8, 10-dideazatetrahydro folic acid | 100 |
| Lactose | 400 |

The 8,10-dideazatetrahydro folic acid is passed through a mesh sieve, mixed with lactose previously sieved and fitted into cachets of suitable size so that each contains 500 mg.

EXAMPLE 6

| Intramuscular injection (sterile suspension in aqueous vehicle) | Mg |
|---|---|
| 8, 10-dideazatetrahydro folic acid | 10 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

EXAMPLE 7

| Intraperitoneal intraveneous or subcutaneous injection (sterile solution in aqueous carrier system) | Mg |
|---|---|
| 8, 10-dideazatetrahydro folic acid | 15 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

The 5,6,7,8-tetrahydropyrido[2,3-d]pyrimidines IB of Taylor et al, U.S. Pat. No. 4,684,653 are in effect structural isomers of the compounds of the present invention, in that the NH group of the tetrahydropyrido ring of the pyrimidine is in the meta position with respect to the L-glutamic acid group, as compared to the ortho position in the compounds of the present invention. In Tables 5 and 6 at column 4, Taylor et al give data showing that N-(4-[2-(2-amino-4-hydroxy-5,6,7,8-tetrahydropyrido[2,3-d]pyrimidin-6-yl)-ethyl]benzoyl)-L-glutamic acid maintains good activity against L1210 leukemia which is comparable to methotrexate, and is a weak inhibitor of dihydrofolate reductase, properties similar to those acknowledged in the present application for the present compounds.

There are significant differences in the ring positions of the various substituent groups in the Taylor et al compounds, as compared to the pteridine ring in the compounds of the present invention.

In the compounds of the invention, there is an NH group in the 5-position of the pteridine ring, whereas in the Taylor compounds this group is present in the 8-position, shifted from the ortho to the meta position with respect to the L-glutamic acid group.

This change in position represents a significant change in the spatial symmetry of the compounds, and it is the spatial orientation of the important substituent groups that in large measure determines pharmacological or therapeutic activity. These spatial changes in fact result in the compounds of the invention having a significantly different pharmacological or therapeutic activity.

There are major differences in cytotoxic potency, the focus of cytotoxic action, and pharmacokinetics. This has shown that no predictions can be made as to the effect of this structural change on the biological effects of these compounds. One could not predict the effect of changing the 8-NH substituent in the Taylor compounds to the 5-position, as it is found in the compounds of the invention.

This change in position leads to differences in electronic properties, especially as effecting bonding between the 4-OH, 4-$NH_2$ and the 5-N atom. These differences are magnified when dealing with the B ring tetrahydro analogues.

In fact, 5, 10-dideaza $FH_4$ (DDTHF, Taylor's agent) is a potent inhibitor of GAR transformylase and a potent cytotoxin; 5, 8, 10-trideaza $FH_4$ is devoid of enzyme or cytotoxic action, while compounds of this invention are devoid of GAR transformylase inhibition but are potent cytotoxic agents. These gross differences among these isosteric or regioisomeric analogues clearly illustrate inability to generalize in this area of structure-activity.

The following experiments demonstrate this.

GROWTH INHIBITION ASSAY FOR L1210 CELLS

Murine L1210 cells were obtained as intraperitoneal ascites suspensions from $BD2F_1$ mice. The cells were grown in RPMI 1640 medium supplemented with 10% fetal calf serum. Cultures in the logarithmic stage of growth were harvested, resuspended and exposed to test compounds at varying concentrations. Growth of controls was monitored to verify that the growth pattern was normal. At 72 hours cell counts were taken and averaged and the means were plotted against drug concentration to determine the concentration causing 50% inhibition of cell growth.

This assay was used to evaluate the five test compounds shown in Table I below of which Nos. 3 to 5 had the general formula:

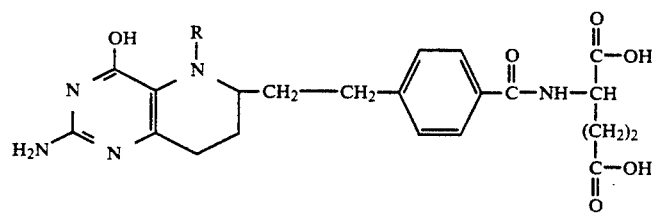

where R is as shown in Table I. The activities for cell growth inhibition are shown by the data in Table I:

TABLE I

| | Compound | R | Growth inhibition L1210 $IC_{50}$ nanomolar (nM) |
|---|---|---|---|
| 1 | Control MTX methotrexate | | 4.3 |
| 2 | Taylor et al 5, 10-DDTHF | | 42 |
| 3 | Compounds | H | 96.8 |
| 4 | of the | $CH_3$ | 38.2 |
| 5 | invention | CHO | 657 |

Inhibition of the glycinamide ribotide formyl transferase (FGAR) and amino-imidazole carboxamide ribotide formyl transferase (AICAR) enzymes was determined by the following test procedure.

ENZYME ASSAYS FOR FGAR AND AICAR

FGAR

Lactobacillus casei extract protein (20 μg) is incubated with 45 μmol of Tris-HCl buffer; pH 7.5, 90 μmol of 2-mercaptoethanol, 0.20 μmol of α,β-glycineamideribotide and 50 nmol of (6R)-10-formyltetrahydrofolate in 0.9 ml for 1 minute at 30° C. The formation of tetrahydrofolate is followed by change in the ultraviolet maximum at 298 nm. For assay of inhibition the test compounds are added along with the 6R-10-formyl FAHy and the concentration that inhibits the reaction by 50% ($IC_{50}$) is determined.

AICAR

AICAR is assayed by the same procedure used for FGAR except that 22 μmol of potassium chloride is included and the substrate is 50 nmol of aminoimidazolecarboxamide ribotide with incubation at 37° C. The quantity of B. casei extract protein utilized is 80 μg.

The data obtained are shown in Table II:

| Compound | | R | $IC_{50}$ (μM) FGAR | AICR |
|---|---|---|---|---|
| 2 | Taylor et al 5, 10-DDTHF | | 0.011 | — |
| 3 | Compounds of the invention | H | >40 | >40 |
| 4 | | $CH_3$ | 53 | >50 |

The Taylor et al compound is clearly an inhibitor of FGAR, but the compounds of the invention are much less effective. While it is not clear what enzyme is being affected, the compounds of the invention are more potent than the Taylor compound (38.2 nM vs. 42 nM).

Having regard to the foregoing disclosure, the following is claimed as inventive and patentable embodiments thereof:

1. 8, 10-dideazatetrahydro folic acid compounds having the formula:

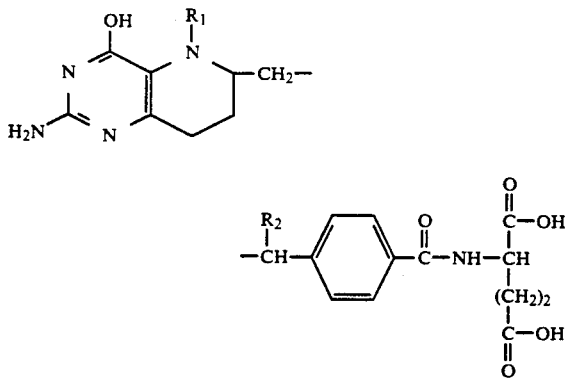

where $R_1$ and $R_2$ are selected from hydrogen and alkyl having from one to about eight carbon atoms; and the carboxylate and acid addition salts thereof.

2. 8, 10-dideazatetrahydro folic acid compounds according to claim 1 in which $R_1$ is hydrogen and $R_2$ is alkyl.

3. 8, 10-dideazatetrahydro folic acid compounds according to claim 2 in which the alkyl is methyl.

4. 8, 10-dideazatetrahydro folic acid compounds according to claim 1 in which $R_1$ and $R_2$ are each hydrogen.

5. 8, 10-dideazatetrahydro folic acid compounds according to claim 1 in which $R_1$ and $R_2$ are each alkyl.

6. A pharmaceutical composition in dosage unit form for treating leukemia or an ascites tumor comprising an amount per dosage unit within the range from about 0.1 to about 500 mg of an 8, 10-dideazatetrahydro folic acid compound according to claim 1, therapeutically effective to treat leukemia or the ascites tumor, together with a pharmaceutically acceptable nontoxic carrier or diluent therefor.

7. A pharmaceutical composition according to claim 6 in which the 8, 10-dideazatetrahydro folic acid is in the form of a pharmaceutically acceptable acid addition salt.

8. A pharmaceutical composition according to claim 6 in which the 8, 10-dideazatetrahydro folic acid is in the form of a pharmaceutically acceptable carboxylate.

9. A pharmaceutical composition according to claim 6 in tablet form.

10. A pharmaceutical composition according to claim 6 in capsule form.

11. A pharmaceutical composition according to claim 6 in suppository form.

12. A pharmaceutical composition according to claim 6 in cachet form.

13. A pharmaceutical composition according to claim 6 in sterile aqueous form.

14. A process for treating leukemia and ascites tumors which comprises administering to a warm-blooded animal having an abnormal proportion of leukocytes constituting a leukemic state, a therapeutic and relatively nontoxic dosage unit amount within the range from about 0.1 mg to about 500 mg per day of an 8, 10-dideazatetrahydro folic acid compound according to claim 1, effective to treat leukemia or ascites tumors.

15. A process according to claim 14 in which the 8, 10-dideazatetrahydro folic acid compound is administered as a pharmaceutically acceptable acid addition salt thereof.

16. A process according to claim 14 in which the 8, 10-dideazatetrahydro folic acid compound is administered as a pharmaceutically acceptable carboxylate.

17. A process according to claim 14 in which the 8, 10-dideazatetrahydro folic acid compound is administered in an amount within the range from about 0.1 to about 500 mg per day.

18. A process according to claim 14 in which the 8, 10-dideazatetrahydro folic acid compound is administered with an inert diluent or carrier.

19. A process according to claim 14 in which the 8, 10-dideazatetrahydro folic acid compound is administered orally.

20. A process according to claim 14 in which the 8, 10-dideazatetrahydro folic acid compound is administered parenterally.

* * * * *